US00PP09357P

United States Patent [19]

Olesen et al.

[11] Patent Number: Plant 9,357

[45] Date of Patent: Nov. 7, 1995

[54] HYBRID TEA ROSE PLANT NAMED 'POULVUE'

[75] Inventors: Pernille Olesen; Mogens N. Olesen, both of Fredensborg, Denmark

[73] Assignee: DeVor Nurseries, Inc., Watsonville, Calif.

[21] Appl. No.: 346,621

[22] Filed: Nov. 30, 1994

[51] Int. Cl.[6] ..... A01H 5/00

[52] U.S. Cl. ..... Plt./11

[58] Field of Search ..... Plt./11, 16, 17

[56] References Cited

U.S. PATENT DOCUMENTS

| | | | |
|---|---|---|---|
| P.P. 2,300 | 11/1963 | Boerner | Plt./11 |
| P.P. 3,431 | 1/1974 | Warriner | Plt./11 |
| P.P. 6,317 | 10/1988 | Warriner | Plt./11 |
| P.P. 8,414 | 10/1993 | Winchel | Plt./11 |
| P.P. 8,700 | 8/1994 | Christensen | Plt./11 |

*Primary Examiner*—Howard J. Locker

*Attorney, Agent, or Firm*—Christie, Parker & Hale

[57] ABSTRACT

A new Hybrid Tea rose plant producing orange peach flowers with yellow reverse.

1 Drawing Sheet

SUMMARY OF THE INVENTION

The present invention relates to a new and distinct variety of rose plant of the Hybrid Tea rose class which was originated by my crossing as seed and pollen parents two unnamed and undistributed seedlings of our creation. The varietal denomination of this new rose is 'Poulvue'.

Among the novel characteristics possessed by this new variety which distinguish it from its parents and all other varieties of which I am aware are its attractive well formed flowers of unusual bicoloration borne on a vigorous plant.

Asexual reproduction by budding of the new variety as performed in Watsonville, Calif., shows that the foregoing and other distinguishing characteristics come true to form and are established and transmitted through succeeding propagations. Other typical forms of asexual reproduction may be also employed.

BRIEF DESCRIPTION OF ILLUSTRATIONS

The accompanying illustrations show typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent.*—Unnamed, unpatented seedling.

*Pollen parent.*—Unnamed, unpatented seedling.

Class: Hybrid Tea.

The following is a detailed description of the new variety, from specimens grown outdoors in Watsonville, Calif., in the month of September. The color terminology used is in accordance with the Royal Horticultural Society Colour Chart (RHSCC), and refers to plate numbers in the aforementioned color chart. Phenotypic expression may vary depending on light, environmental and cultural conditions.

FLOWER

Blooming habit: Recurrent.

A. Bud:

(1) *Size.*—Medium, about 2.5 cm to about 3.5 cm long and about 1.5 cm to about 2.5 cm wide.

(2) *Form.*—Pointed, ovoid.

(3) *Color.*—When sepals first divide, bud color is near 11B with near 53B veining and edging.

(4) *Sepals.*—Upright, about 3 cm to about 5.5 cm covering bud, then unfurl when about ⅓ open and spread; some sepals are foliaceous. Color: Sometimes near 146A on edges and near 146C in center.

(5) *Peduncle.*—Length: About 14–16 cm. Aspect: Smooth. Strength: Erect, sturdy. Color: Near 143B.

(6) *Bracts.*—None.

B. Bloom:

(1) *Size.*—Average size when fully expanded — about 9 cm to 11 cm.

(2) *Borne.*—Singly, one to a stem.

(3) *Form.*—Imbricated with reflexed petals.

(4) *Petalage.*—Number of petals under normal conditions — about 40 to 45.

(5) *Color* (⅓ *to* ½ open).— Outer petals — Top Surface: Very tip of petal has a touch of near 53A; ½ of petal near 43D becoming near 33C towards bottom; base near 9A; Undersurface: Top edge is near 53D; top third of petal is near 20D deepening to near 10A; base deepens to near 9B. Inner Petals — Top Surface: Top ½ of petal is near 33C changing to near 32C and proceeding to near 32B; base is near 9A; Undersurface: Top has slight edging of near 51B; top third of petal is near 14C deepening to near 9B with base near 9A. Base of petals — (point of attachment): Yellow group 9A. General tonality from a distance: Pink-orange-yellow blend.

(6) *Color* (*fully open*)—Outer petals — Top surface: Top ½ is near 33D changing to near 25C; base of petal is near 9A; Undersurface: Top ⅓ is near 18B changing to near 15D; base is near 9B. Inner petals — Top surface: Top ¾ is near 31C changing to near 26C changing to near 9C; base is near 9B; Undersurface: Top has slight edging of near 33B; top ½ is near 20C changing to near 11B fading to near 9C; base is near 9A. Base of petals: (point of attachment): Near 9A. General tonality from a distance: Orange to peach — yellow blend.

(7) *Color change.*— As bloom ages: Outer petals fade to a lighter color while the inner petals retain their intense color. Petal top surface: All of the petal fades to a lighter color but the base retains its intense color. Petal undersurface: All of the petals fades to a lighter color but the base retains its intense color. General tonality at a distance: Peach-yellow blend.

C. Petals:

(1) *Texture.*—Medium thick.

(2) *Appearance.*—Inside semi-velvety and outside matte.

(3) *Form.*—Wedge-shaped with curled apex.
(4) *Arrangement.*—Imbricated.
(5) *Petaloids.*—Few.
(6) *Fragrance.*—Piquant perfume.
(7) *Lasting quality.*—On plant about 10–14 days.
(8) *Persistence.*—Petals drop off cleanly.

REPRODUCTIVE ORGANS

A. Stamens:
(1) *Arrangement.*—Irregularly arranged around styles.
(2) *Anthers.*—Color near 14C.
(3) *Filaments.*—Color-base and tip near 14B, balance near 33B.
(4) *Pollen.*—Color — near 14C.

B. Pistils:
(1) *Styles.*—Bunched, even, medium length.
(2) *Stigmas.*—Color near 10B.

C. Characteristics of hips: Not observed.

PLANT

A. Form: Upright.

B. Growth: Vigorous; height attained about 60 cm to about 100 cm at first season.

C. Foliage: Compound 3, 5 and 7 leaflets.
(1) *Size.*—Medium, about 6.5 cm long and about 3.5 cm wide.
(2) *Quantity.*—Abundant.
(3) *Color.*—New foliage — upper side near 147A with overlay of near 178B on edges; underside near 147B overlayed with near 178A; mature foliage — upper side near 147A, underside near 147B.
(4) *Shape.*—Oval.
(5) *Texture.*—Upper side leathery, semi-glossy, smooth; underside leathery, smooth.
(6) *Edge.*—Serrate.
(7) *Serration.*—Denticulate.
(8) *Leaf stem.*—Color — medium green.
(9) *Stipules.*—About 1.5 cm, slightly glandular, adnate and parallel.
(10) *Rachis.*—Small prickles on underside.
(11) *Petioles.*—Top near 146B, underside near 146C.
(12) *Auricle.*—Thin, reflexing, with glands on edges.
(13) *Resistance to disease.*—Very resistant to black-spot, mildew and rust.

D. Wood:
(1) New wood.—Color near 146C with near 183D cast, bark smooth.
(2) Old wood.—Color near 146C, bark smooth.

E. Flower stem: About 28 cm to about 38 cm from last cut.

F. Thorns:
*Quantity.*—On main stalk, average laterals from stalk, some.
*Form.*—Slightly curved downward, wing-shaped.
*Length.*—Medium, about 0.5 mm to about 1 mm.
*Color.*—Near 153D.
*Position.*—Irregular.
*Prickles.*—Some.

G. Winter hardiness: Winter hardy in Denmark and in Watsonville, Calif.

I claim:

1. A new and distinct variety of rose plant of the Hybrid Tea rose class, as shown and described.

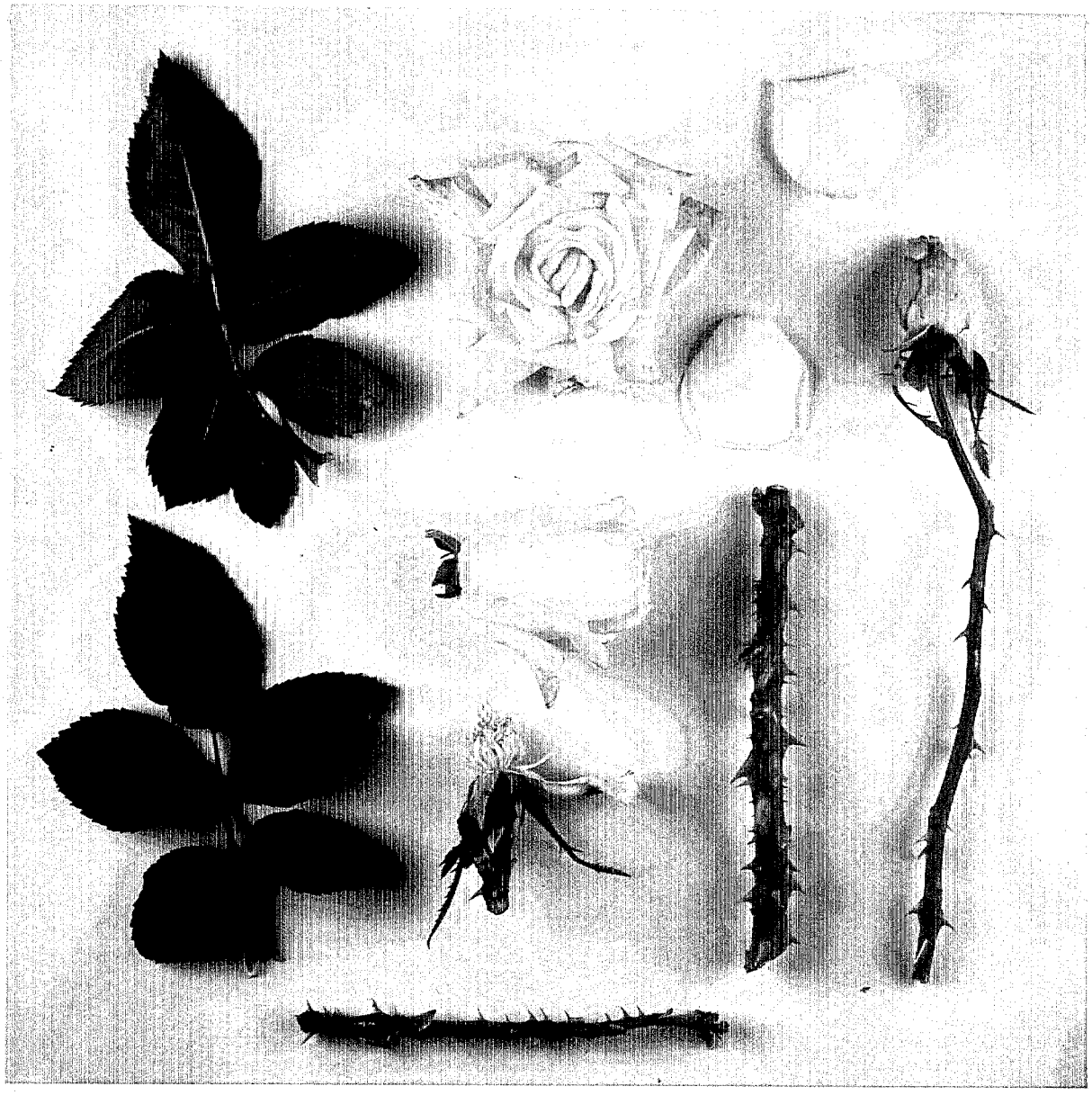

* * * * *